United States Patent
O'Carroll et al.

(10) Patent No.: US 11,160,549 B2
(45) Date of Patent: *Nov. 2, 2021

(54) MEDICAL SECURING DEVICE FOR SECURING AN OBJECT WITH A SECURING MEMBER

(71) Applicant: Medtentia International Ltd Oy, Espoo (FI)

(72) Inventors: Ger O'Carroll, Collooney (IE); Jake O'Regan, Collooney (IE); Kieran Cafferkey, Collooney (IE); Hans-Reinhard Zerkowski, Kreuzlingen TG (CH); Olli Keränen, Bjärred (SE)

(73) Assignee: Medtentia International Ltd. Oy, Espoo (FI)

( * ) Notice: Subject to any disclaimer, the term of this patent is extended or adjusted under 35 U.S.C. 154(b) by 168 days.

This patent is subject to a terminal disclaimer.

(21) Appl. No.: 16/014,042

(22) Filed: Jun. 21, 2018

(65) Prior Publication Data

US 2018/0368830 A1    Dec. 27, 2018

(30) Foreign Application Priority Data

Jun. 22, 2017    (EP) .................................. 17177402

(51) Int. Cl.
*A61B 17/04* (2006.01)
*A61B 17/06* (2006.01)
(Continued)

(52) U.S. Cl.
CPC ...... *A61B 17/0491* (2013.01); *A61B 17/0401* (2013.01); *A61B 17/0469* (2013.01);
(Continued)

(58) Field of Classification Search
CPC ............ A61B 17/0491; A61B 17/0469; A61B 17/0482; A61B 17/0485;
(Continued)

(56) References Cited

U.S. PATENT DOCUMENTS 5,972,004 A     10/1999  Williamson, IV et al.
10,905,555 B2 *  2/2021  O'Carroll ............... A61B 17/10
(Continued)

FOREIGN PATENT DOCUMENTS

WO    WO2016196579 A1    12/2016

OTHER PUBLICATIONS

European Patent Office, Search report dated Aug. 22, 2017 in EP patent application No. 17177402.9.

*Primary Examiner* — Katrina M Stransky
(74) *Attorney, Agent, or Firm* — Patent Grove LLC; Tomas Friend (57) ABSTRACT

A medical securing device for securing an object with a securing member into a tissue comprises an elongated sheath with proximal and distal ends, and a securing member introduction device having proximal and distal ends. The securing member comprises first and second ends. The distal end of the securing member introduction device is configured to extend the second end of the securing member from the sheath and introduce it to or through the tissue via an introduction movement so to secure the portion of the securing member to the object and/or to the tissue. This is advantageously configured to happen without extending the securing member introduction device through the tissue whereupon no extra hole is made to the tissue by the securing member introduction device.

20 Claims, 7 Drawing Sheets

(51) Int. Cl.
*A61F 2/24* (2006.01)
*A61B 17/068* (2006.01)
*A61B 17/00* (2006.01)
*A61B 17/30* (2006.01)
*A61B 17/064* (2006.01)

(52) U.S. Cl.
CPC ...... *A61B 17/0482* (2013.01); *A61B 17/0485* (2013.01); *A61B 17/068* (2013.01); *A61B 17/06166* (2013.01); *A61F 2/2427* (2013.01); *A61F 2/2466* (2013.01); *A61B 2017/00243* (2013.01); *A61B 2017/00783* (2013.01); *A61B 2017/00867* (2013.01); *A61B 2017/0409* (2013.01); *A61B 2017/0464* (2013.01); *A61B 2017/0472* (2013.01); *A61B 2017/0477* (2013.01); *A61B 2017/0645* (2013.01); *A61B 2017/0649* (2013.01); *A61B 2017/06057* (2013.01); *A61B 2017/306* (2013.01); *A61F 2/2445* (2013.01); *A61F 2220/0008* (2013.01); *A61F 2230/0091* (2013.01)

(58) Field of Classification Search
CPC ........ A61B 2017/0477; A61B 17/0467; A61B 17/0483; A61B 17/062; A61B 2017/0475; A61B 2017/0474; A61B 2017/0472; A61B 2017/047; A61F 2/2427; A61F 2/2466
See application file for complete search history.

(56) References Cited

U.S. PATENT DOCUMENTS

2010/0113873 A1* 5/2010 Suzuki ................ A61B 1/0125
600/106
2011/0270279 A1   11/2011 Badhwar
2014/0058417 A1*  2/2014 Levy .................... A61F 2/0063
606/151

* cited by examiner

MEDICAL SECURING DEVICE FOR SECURING AN OBJECT WITH A SECURING MEMBER

PRIORITY

This application claims priority of EP No. 17177402.9, filed on 22 Jun. 2017 the content of which is incorporated herein by reference.

TECHNICAL FIELD OF THE INVENTION

The invention relates to a medical securing device for securing an object, such as a cardiac implant device (for example annuloplasty ring) or a portion of a tissue with a securing member, such as a suture. In particularly the invention relates to a catheter-operated or cannula-operated medical securing device for securing the cardiac implant device into an annulus of a heart valve, such as a mitral valve or tricuspid valve, comprised of valve tissue and including the annulus and a plurality of leaflets. However, the principle of the invention can also be applied for an open-heart operated medical securing device, as well as securing also other object as only the cardiac implant devices, such as tissue or skin transplant beneath the skin or the like. In addition the invention can also be used for securing an artificial heart valve, as an example.

BACKGROUND OF THE INVENTION

Figures 1A, 1B, 2A, 2B:
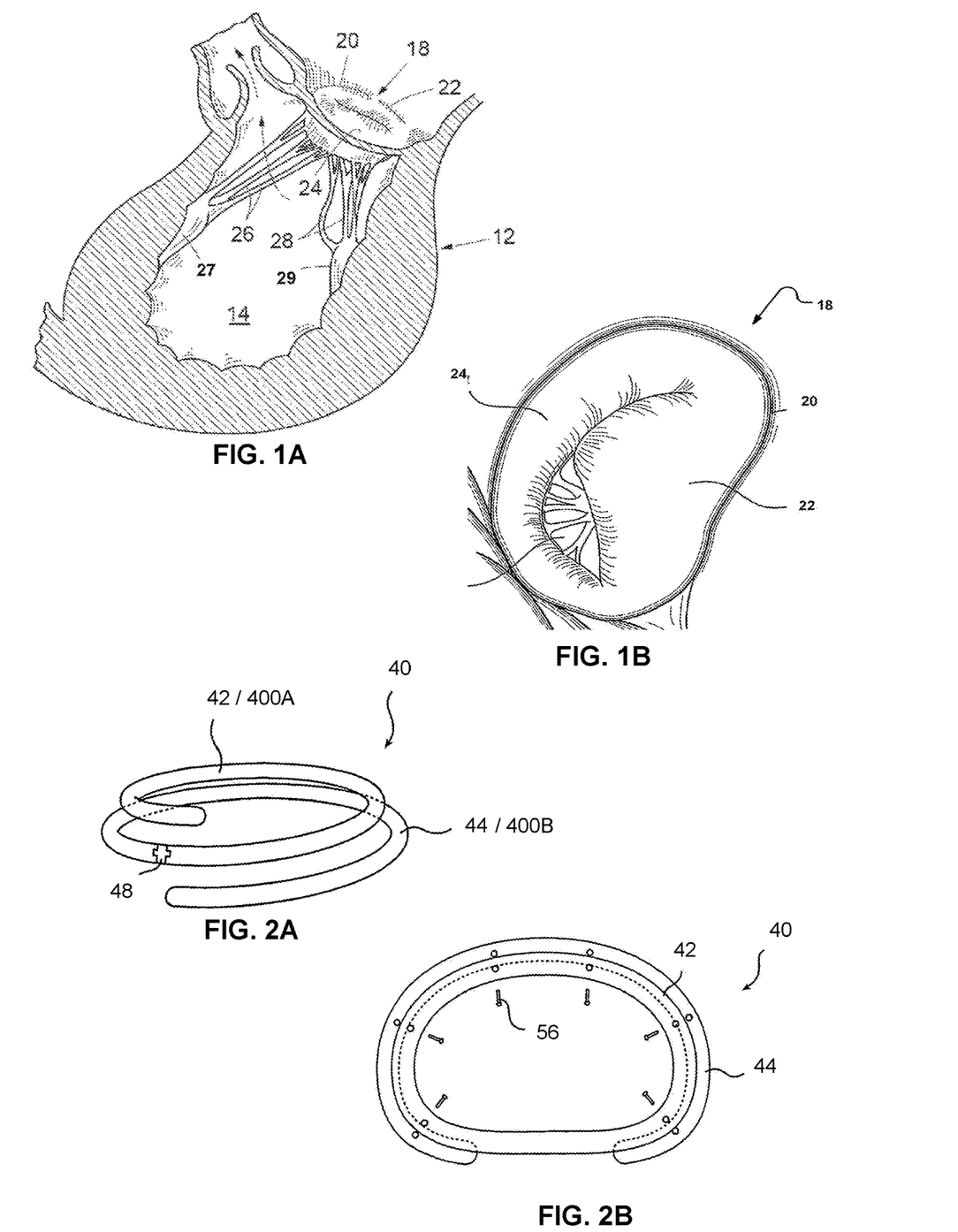
FIGS. 1A-1B illustrate schematically a portion of a heart and mitral valve.
FIGS. 2A-2B illustrate a prior art cardiac implant device for repairing of one or more leaflets of a heart valve.

FIG. 1A illustrates a portion of the heart 12, the mitral valve 18, and the left ventricle 14. The mitral valve is at its boundary circumferenced by an annulus 20. The valve has two cusps or leaflets 22, 24. Each of these cusps or leaflets 22, 24 are connected to a respective papillary muscle 27, 29 via their respective connecting chordae 26, 28. In normal healthy individuals the free edges of the opposing leaflets will close the valve by coaptation. However, for some individuals the closure is not complete, which results in a regurgitation, also called valvular insufficiency, i.e. back flow of blood to the left atrium making the heart less effective and with potentially severe consequences for the patient. FIG. 1B illustrates a mitral valve 18, in which the leaflets 22, 24 do not close properly. This commonly occurs when the annulus 20 becomes dilated. One surgical procedure to correct this is to remove a portion of the leaflet 24 and stitch the cut edges together with one another. The procedure will pull back the annulus 20 to a more normal position. However the strength of the leaflet 24 is altered. Similar problems with a less effective heart function occur if one or both leaflets are perforated to such an extent that blood is flowing towards the left atrium, although the leaflets close properly.

In some conditions of degenerated heart function, the leaflets do not present a solid surface, as in a degenerative valve disease. The leaflet may also be ruptured, most commonly at an edge of a leaflet, resulting in an incomplete coaptation. Hence, cardiac devices and methods are developed for repairing of one or more leaflets of a heart valve, or other related anatomical structures, such as the chordae attached to the ventricular side of leaflets.

FIGS. 2A and 2B illustrate a prior art cardiac implant device and method for repairing of one or more leaflets of a heart valve as is described in the applicant's previous EP-patent (EP 1 853 199 B1), where the device 40 comprises a first and a second loop-shaped support 42, 44, which are connected to each other by means of a connecting part 48 so as to form a coil-shape. The coil-shape of the device is advantageous during insertion, since the device 40 may then be rotated into position, as described in the patent in more details. One of the supports 44 may be open, e.g. C or D or any other anatomical shaped such that the support 44 presents an end to lead the movement of the support 44 when being rotated into position. The position of the supports 42, 44 are secured by fasteners 56, which are inserted and fastened by hand or small screwdriver.

It is found that the prior art cardiac implant devices, such as depicted above, work very well, but there are still some disadvantages relating to the securing of the cardiac device into the annulus of the heart valve. The cardiac devices are typically manually sutured by a traditional needle and yarns, which is time consuming, because in practise it is needed at least seven knots to be tied in order to have even some certainty that the device is secured. In addition, if the device is sutured by one yarn, which has a drawback namely if one or more knots is/are loosen or the yarn is broken, then the whole securing will come loosen or broken.

In addition with the previous suturing devices it has been difficult to suture in the correct position, thereby providing insufficient suturing strength, and also resulting in a very time consuming procedure, which increases the risks for the patient. Previous suturing devices are also not sufficiently compact for catheter based procedures, for example. There is therefore a need to provide an improved suturing device that solves these issues.

The cardiac implant devices can also be secured by screws. However, the screws are very small, the assembling, positioning and controlling of which are extremely difficult. The screws must be inserted through the both the first and second (upper and lower) loop-shaped support portions 42, 44 (tiny holes in both of the portions), which is highly demanding, because if the first screw is tightened too much, it will distort the portions little bit and thus misaligning the other holes and thereby making it impossible to inserting the other screws. Furthermore there is a huge risk to drop the small screws into the cardiac structure, because for example any safety blankets cannot be used. In addition also magnetic material cannot be used due to possible later magnetic imaging.

Overall the securing or anchoring of the object, especially the cardiac implant, to the heart is very demanding, because the heart or ventricle is a closed system which is in addition in motion during the securing or anchoring process. Still the tissue especially in the inner rim of the annulus is very thin, which might be damaged when punctured by the needle and where the hole made by the needle does not close up.

SUMMARY OF THE INVENTION

It is an object of the invention to alleviate and eliminate the problems relating to the known prior art. Especially the object of the invention is to provide a medical securing device for securing an object, such as especially a cardiac implant device with a securing member into a tissue, especially into an annulus of a heart valve in an easy, fast, safe and accurate manner with a high degree of control and so that the tissue is not damaged or at least the operations or handling of the tissue is minimized The object of the invention can be achieved by the features of independent claim.

The invention relates to a medical securing device for securing an object with a securing member into a tissue according to claim 1. The medical securing device may be for example a suturing device for suturing the cardiac implant device into the annulus of the heart valve, but also other objects can be secured, such as other implants or portions of a tissue into a second tissue. The object to be secured may even be a portion of a tissue. The implant can be either artificial implants or natural implants. The cardiac implant device may be any cardiac implant device known from prior art, such as described in FIGS. 1-2 and having ring or double ring (helical) shape especially for mitral implant, but also any further application or other device, like a centrical or atrium or septum correction patch or device or for example a heart valve prosthesis.

According to an embodiment of the invention a medical securing device for securing an object, such as the cardiac implant device or tissue or other object, comprises an elongated sheath extending in a longitudinal direction and having proximal and distal ends. The distal end of the elongated sheath comprises a support portion to support the elongated sheath to the object, such as to the cardiac implant device and/or to the tissue. The medical securing device comprises also a securing member introduction device, like a thrust arm, extending from the sheath and having proximal and distal ends.

The securing member introduction device is configured to extend a securing member having first and second ends from the sheath and introduce at least one end of the securing member through to or into the tissue via an introduction movement so to secure the portion of the securing member to the object and/or to the tissue. At least the second end of the securing member is configured to penetrate the tissue from the proximal side to the distal side, whereupon the first end may be left to the proximal side of the tissue. However, according to an embodiment the securing member introduction device may introduce the both ends of the securing member to the distal side of the tissue so that the loop wire between the ends of the securing member is left to the proximal side of the tissue and advantageously introduced with the object and thereby to secure and anchor said object to the tissue.

It is to be noted that when only one end of the securing member is introduced through the tissue (advantageously in the outer side or posterior side or the object, such as a loop or ring shaped object) the one and only hole to be punctured by the end of the securing member (or needle head of the securing member or of the securing member introduction device) can be located in a desired and optimal location to the tissue, such as to the outer side (posterior side) of the loop or ring shaped object and into the thicker portion of the tissue or in other way in an advantageous location.

According to another embodiment also the first end of the securing member may be configured to penetrate the tissue. In this embodiment the medical securing device may comprise also a second securing member introduction device to extend the first (proximal) end of the securing member from the sheath and into or through the tissue so to secure the portion of the securing member to the object and/or to the tissue. However, it is to be noted that according to an embodiment also only one securing member introduction device may be used to introduce the both ends to the distal side especially when the securing member is stiff enough. The first end of the securing member is advantageously introduced to the other side of the object, such as the cardiac implant device, than the second end of the securing member and so that the loop connecting said ends of the securing member stays in the proximal side of the tissue and is advantageously introduced with the object and thereby secures and anchors said object to the tissue.

According to an embodiment the end of the securing member to be penetrated through the tissue functions as a needle (advantageously comprises a needle head), whereupon there is no need to extend the securing member introduction device through the tissue. Thereby no extra hole is made to the tissue by the securing member introduction device, which is clear advantage, namely the securing member, such as a suture, fulfils the aperture when it penetrates through the tissue because it will remain there also after the penetration.

Alternatively the end of the securing member may comprise a cap like end and opening in it, whereupon the distal end of the securing member introduction device is configured to elongate through the opening in the securing member end. In this embodiment the distal end of the securing member introduction device is configured to function as a needle (advantageously comprises a needle head). Also in this embodiment no extra hole is made to the tissue since the securing member, such as suture, fulfils the aperture when it penetrates through the tissue because it will remain there also after the penetration. In addition it is to be noted that the cap like end of the securing member may be at least partially compressible such as a shuttlecock, whereupon it can compress when introduced through the tissue an again take the original form after penetration. In addition the end portion may be configured to elongating to a certain predetermined direction after penetration the tissue. In these ways the securing member does not enlarge the hole in the tissue made by the securing member introduction device but at the same time it is ensured that the enlarged cap like end of the securing member will not slip back to the proximal side.

In both embodiments the end of the securing member advantageously comprises an increased diameter portion to secure the end in question to the object and/or to the tissue or in order to enable easy catch of the end by a retrieval device, if the retrieval device is used for catching the end of the securing member.

According to an embodiment at least the second end or the second (distal) portion of the securing member comprises shape memory material, whereupon the at least the second end or the second portion of the securing member is configured to be twisted due to shape memory material when released by the securing member introduction device and thereby coupled with the object and securing the portion of the securing member to the object and/or to the tissue. Advantageously the second end or the second portion of the securing member is resiliently biased to move towards a desired direction, so towards the object or tissue, for example. Naturally also the first end or the first (proximal) portion of the securing member may comprise shape memory material, whereupon it is also configured to be twisted to the desired direction after releasing.

The securing member may also comprise dual memory feature so that the first shape memory feature will turn the ends of the securing member against each other, especially when the both ends of the securing member are introduced through the tissue to the distal side, and the second shape memory feature will twist and wrap the ends of the of the securing member around each other.

According to an embodiment the medical securing device may also comprise a retrieval device at a distal end thereof. The retrieval device may be implemented as a catheter having a needle or tip portion configured to penetrate or puncture into or through the tissue. When the retrieval device is extended through the tissue, the retrieval device advantageously captures a portion of the securing member, such as a portion of the suture or other securing member portion disclosed elsewhere in this document. After capturing the portion of the securing member, the medical securing device is used for securing the object, such as the cardiac implant device by the securing member (or at least by portion of it) to the tissue, like the annulus of the valve.

The retrieval device, such as the needle head of the securing member or the end portion of the securing member introduction device can have different types of tip portions, and may comprise either linear or pre-curved needle, for example. For instance, the tip portion may be configured for penetrating and/or puncturing into or through the tissue. In addition the tip portion may be formed or arranged so that it guides and directs the tip portion in a certain angle or track or path, which can also be a curved track or path depending on the form of the tip, for example. Additionally, using of an atraumatic type tip portion is very advantageous namely it does not cut the tissue as such but rather it penetrates between the tissue fibers and displaces them making no cut into the tissue. In addition if the tip portion is pre-curved it also additionally facilitate to manage the trajectory of the distal end of the securing member introduction device and/or retrieval device in a natural way.

However, the form and type of the tip portions can be selected depending on the application, and can be for example a cutting needle, if there is need to puncture the skin and for example securing a tissue or skin transplant beneath the skin.

In addition, depending on the application the securing member may be a suture, wire, staple, helical clip, locking clip, spring clip, or circular clip, and comprising shape memory material, metal or polymer or other suitable material. In embodiments describing the current invention the suture and wire is used as an advantageous example of the securing member. However it should be understood that also other type securing members can be used and these are only examples.

In addition according to an embodiment the first and/or second end of the securing member introduction device is mechanically coupled with the securing member and arranged to be released from the securing member for example by turning the securing member introduction device around the longitudinal axis of the securing member introduction device a certain amount. This can be implemented e.g. by a suitable slot or groove and corresponding pin so that when the securing member introduction device is turned e.g. 90 degrees the pin is released from the slot or groove and thus the securing member is released. In addition as an example the releasing can also be implemented by other maneuvers, like by directional guiding or guidance of the securing member introduction device where the securing member is just pushed by the introduction device and the releasing occurs just when the introduction device is retracted backwards and no turning or other maneuver is needed. It is to be noted that by turning e.g. into the opposite direction the object can be still positioned in a more advantageous position or location for securing.

According to an embodiment the medical securing device may comprise also an actuating member coupled with the securing member introduction device and/or retrieval device, so to extend or output from the sheath, for example. The actuating member may be configured to provide a back-and/or-forth (so out and/or in) movement of the securing member introduction device(s) and/or the retrieval device (if used), when operated. Advantageously the actuating member is managed at the proximal end of the medical securing device and outside a patient to be operated. However, it is to be noted that the actuating member can be located and operated in principle anywhere in connection with the device and that the invention is not limited to only to examples described literally.

The medical securing device may comprise also a spring or pre-stringed spring or a pressure accumulator, which can help the operation of the actuating member. For example, according to an embodiment the medical securing device comprises an operation member and the pre-stringed spring or pressure accumulator coupled with the actuating member. When the operator manipulates, such as press, the operation member, it controls the pre-stringed spring or pressure accumulator, which again pushes the securing member introduction device(s) and/or retrieval device (if used) outside the sheath. In addition the medical securing device may comprise a second pre-stringed spring or pressure accumulator, which again retracts the securing member introduction device(s) and/or retrieval device (if used) inside the sheath after securing operation or in order to finalize the securing operation. It is to be noted that both the securing member introduction device and retrieval device can have own separately operated actuating members. In addition the actuating member can be implemented by a hydraulic or pneumatic arrangement whereupon there is a hydraulic or pneumatic hose, for example, conducting and inducing the pressing and retracting force to the securing member introduction device and/or retrieval device under operation.

When the actuating member are operated automatically or semi-automatically, the operator can focus to more important tasks, such as for addressing and focusing the distal end of the medical securing device to an appropriate position, which is a clear advantage. In addition according to an embodiment the operation of the actuating member may be as a single back-and-forth movement of the securing member introduction device and/or retrieval device, or alternatively the operation may comprise a number of back-and-forth movements.

The present invention offers advantages and superiority over the known prior art, such as an easy, safe, precise and time saving manner to reliable securing the object to the tissue, such as the cardiac implant device into the annulus of the valve with the securing member. In addition, the present invention provides for a compact medical securing device, such as a suturing device, that facilitates suturing and fixation of objects, such as a cardiac implant device, especially an annuloplasty implant, to the tissue. It is to be noted that also portion of the tissue can be secured into other tissue or portion of the tissue, as well as skin transplants can also be secured just beneath the skin Furthermore it is particularly easy to suture or secure beneath a tissue wall, such as the annulus of a heart valve, from the opposite side facing an operator, which otherwise is cumbersome due to the limited visibility or in case of no visibility. The compact medical securing device allows it to be catheter deliverable for a minimally invasive procedure. Furthermore, when using the catheter-operated or cannula-operated medical securing device, risks for having any medical drawbacks or symptoms are much lower than e.g. in the traditional open-heart operation. Also the patient recovery process is much faster. In addition the using of the medical securing device according to the present invention is very clear, logical and straight for the user, namely the securing operation can be done advantageously by one continuous movement.

In addition when only one end of the securing member is introduced through the tissue, the optimal location of the tissue can be easily selected and only one hole is made to the tissue.

The exemplary embodiments presented in this text are not to be interpreted to pose limitations to the applicability of the appended claims. The verb "to comprise" is used in this text as an open limitation that does not exclude the existence of also unrecited features. The features recited in depending claims are mutually freely combinable unless otherwise explicitly stated.

The novel features which are considered as characteristic of the invention are set forth in particular in the appended claims. The invention itself, however, both as to its construction and its method of operation, together with additional objects and advantages thereof, will be best understood from the following description of specific example embodiments when read in connection with the accompanying drawings.

BRIEF DESCRIPTION OF THE DRAWINGS

Next the invention will be described in greater detail with reference to exemplary embodiments in accordance with the accompanying drawings, in which:

FIGS. 7A-8E illustrate examples of the medical securing device with retrieval devices according to advantageous embodiment of the invention, FIGS. 9-12 illustrate example additional features of the medical securing device according to advantageous embodiments of the invention.

DETAILED DESCRIPTION

FIGS. 1A-1B and 2A-2B are already discussed in more details in connection with the background of the invention portion above.

Figure 3A:
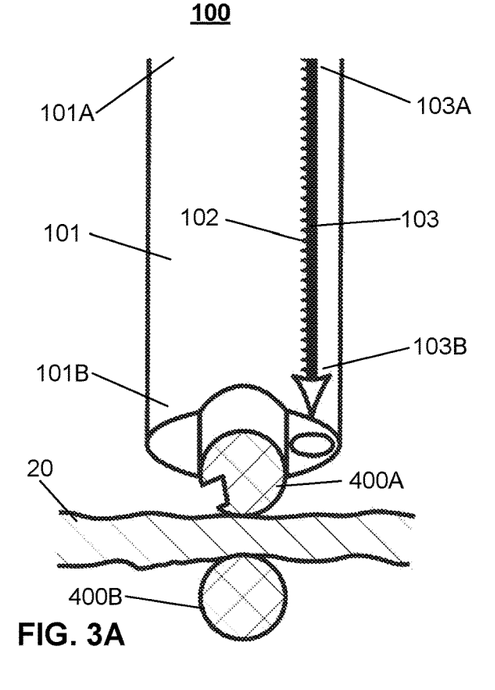
FIGS. 3A-3D illustrate an example of the medical securing device according to advantageous embodiment of the invention.
Figure 3B:
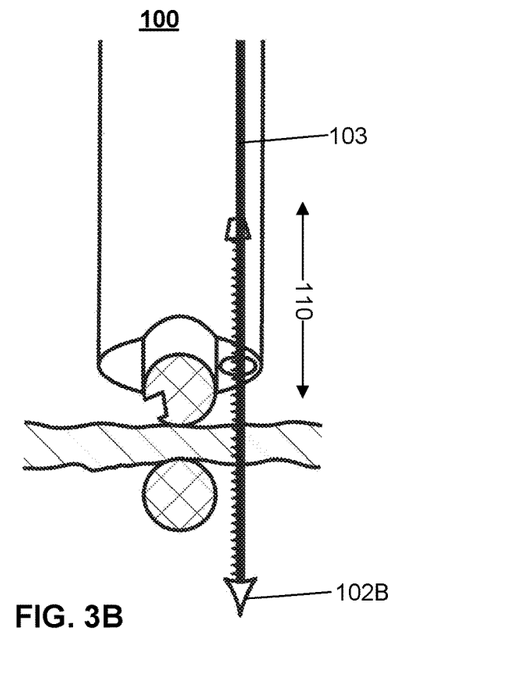
Figure 3C:
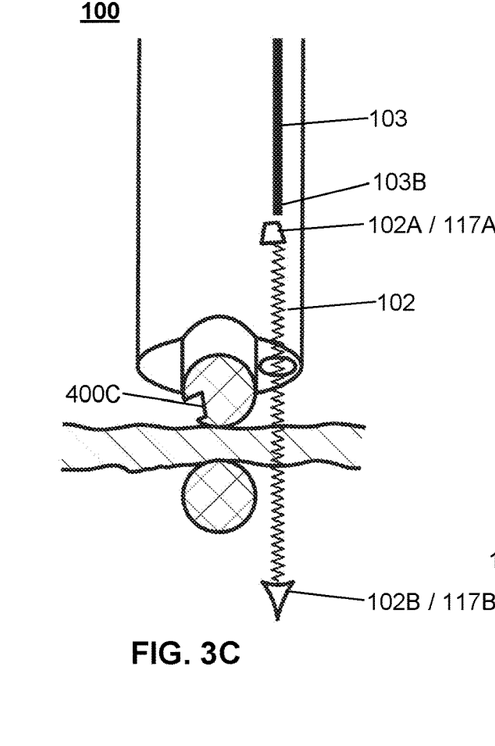
Figure 12:
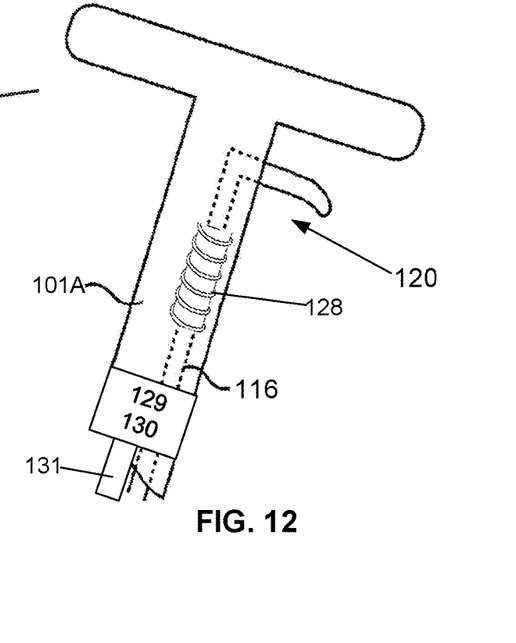

FIGS. 3A-3D illustrate an example of the medical securing device 100 according to advantageous embodiment of the invention for securing an object 400A, 400B with a securing member 102 into a tissue 20. The medical securing 100 device comprises an elongated sheath 101 comprising proximal 101A and distal 101B ends, and a securing member introduction device 103 advantageously inside the elongated sheath 101. Also the securing member 102 is advantageously inside the elongated sheath 101 at the beginning (FIG. 3A). Also the securing member introduction device 103 comprises proximal 103A and distal 103B ends and is configured to be controlled by an operator advantageously from the proximal end of the medical securing device 100 (as shown in FIG. 12, for example).

The securing member 102 comprises first 102A and second 102B ends, where the second end 102 is configured to be introduced through the tissue by a movement 110 of the securing member introduction device 103. In more details the distal end 103B of the securing member introduction device 103 is configured to extend the second 102B end of the securing member 102 from the sheath 101 and introduce it into or through the tissue 20 via said introduction movement 110 so to secure the portion of the securing member 102 to the object 400A, 400B and/or to the tissue 20.

As can be seen in FIGS. 3A-3D the second end (distal) 102B of the securing member 102 functions as a needle and according to an embodiment comprises a needle head, and is thereby configured to penetrate the tissue 20 when extended by the movement of the securing member introduction device 103. In this embodiment the securing member introduction device 103 does not have a needle head and thus does not make any hole to the tissue 20 but the securing member introduction device 103 only extends the second end 102B of the securing member though the tissue.

Figure 3D:
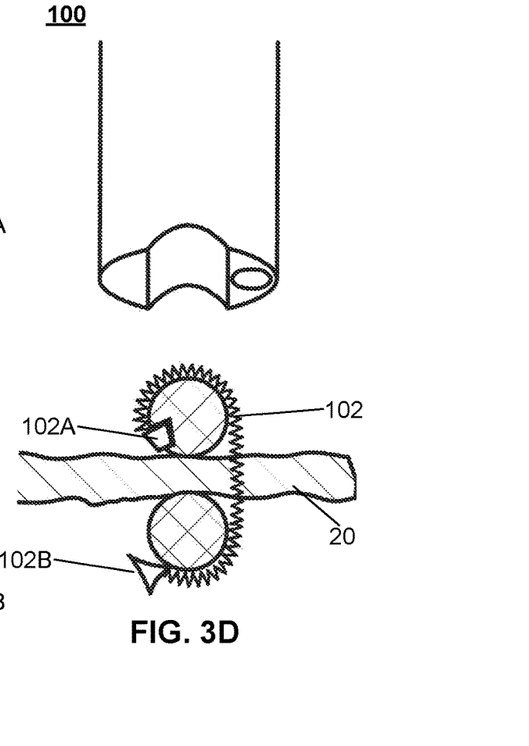
Figure 4A:
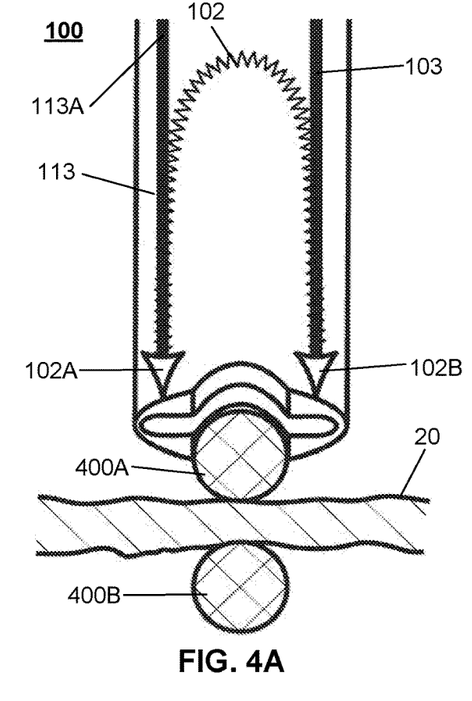
FIGS. 4A-4D illustrate another example of the medical securing device according to advantageous embodiment of the invention.
Figure 4B:
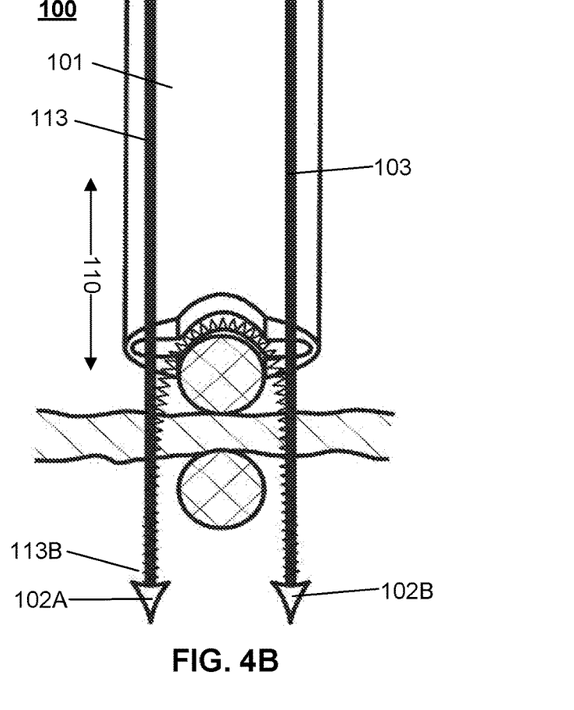
Figure 4C:
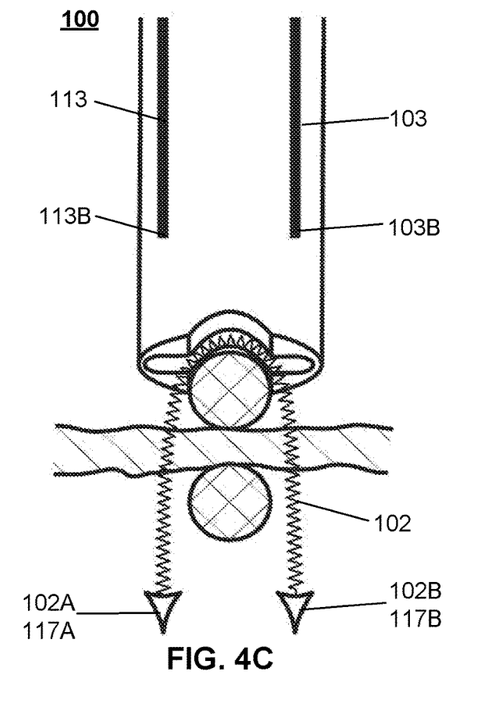
Figure 4D:
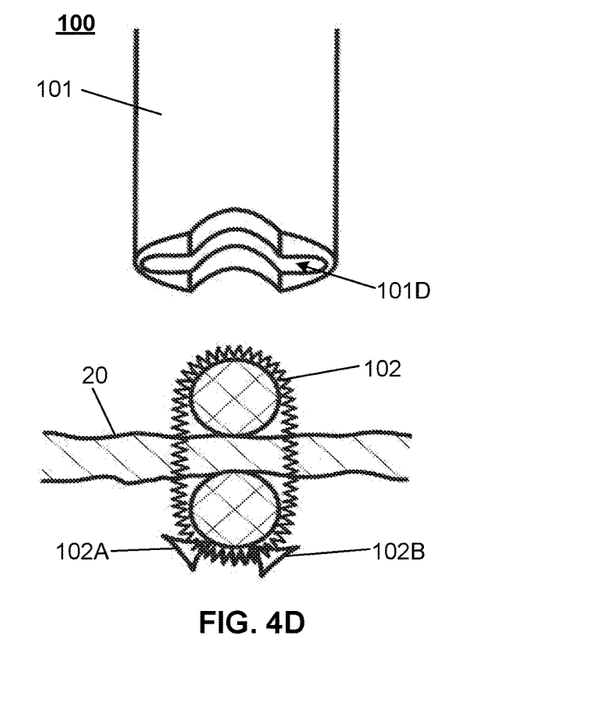
Figure 5A:
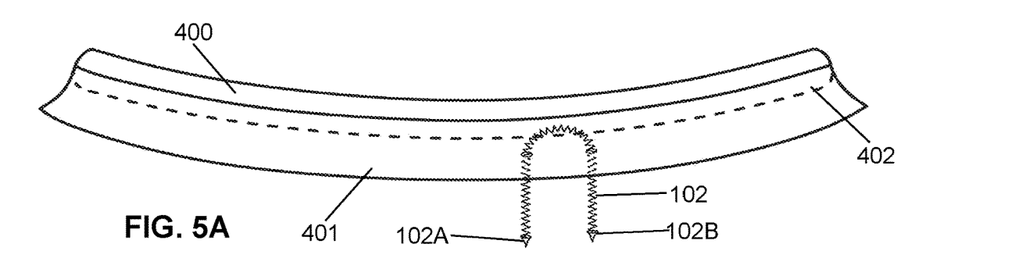
FIGS. 5A-5D illustrate an example about the securing of an object according to advantageous embodiment of the invention.
Figure 5B:
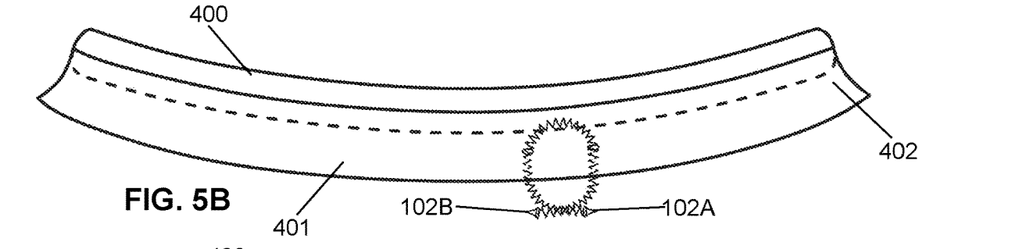
Figure 5C:
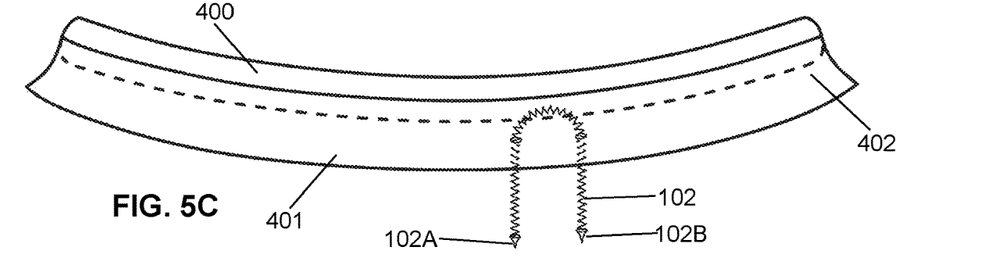
Figure 5D:
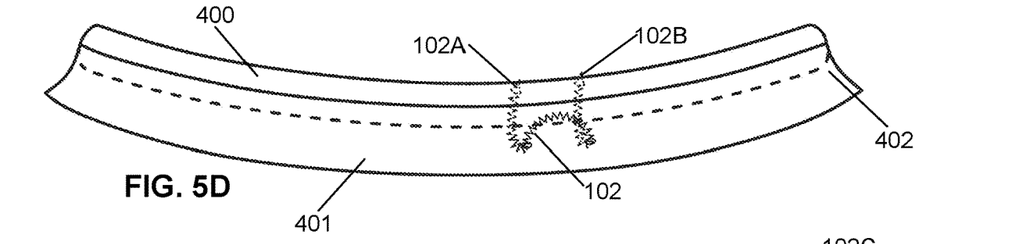

Advantageously the second 102B end or the second (distal) portion of the securing member 102 comprises shape memory material, whereupon the second end 102B or the second portion of the securing member 102 is configured to be turned and/or twisted due to shape memory material when released by the securing member introduction device 103, as can be seen in FIG. 3D. Advantageously also the first end 102A or the first (proximal) portion of the securing member 102 comprises also shape memory material, whereupon also the first end 102A or the first portion of the securing member 102 is configured to be turned and/or twisted when released by the securing member introduction device 103, as can be seen in FIG. 3D. Advantageously the portions 102A, 102B of the securing member 102 are resiliently biased so to move towards the object 400A, 400B or tissue 20 due to shape memory material and thereby couple with the object 400A, 400B and securing the portion of the securing member 102 to the object 400A, 400B and/or to the tissue 20.

At least one of the end portions 102A, 102B of the securing member 102 comprises advantageously an increased diameter portion 117A, 117B so to secure the end in question to the object 400A, 400B and/or to the tissue 20 more tightly or secured way. According to an example the object 400A, 400B may even comprise a recess 400C or the like to receive the increased diameter portion 117A, 117B and thereby secure it more tightly.

FIGS. 4A-4D illustrate another example of the medical securing device 100 according to advantageous embodiment of the invention for securing an object 400A, 400B with a securing member 102 into a tissue 20, where the medical securing device 100 comprises in addition a second securing member introduction device 113 advantageous inside the elongated sheath 101. The second securing member introduction device 113 comprises also proximal 113A and distal 113B ends, wherein the distal end 113B of the second securing member introduction device 113 is configured to extend the first 102A end of the securing member 102 from the sheath 101 and into the or through the tissue 20 so to secure the portion of the securing member 102 to the object 400A, 400B and/or to the tissue 20. Advantageously the first 102A end of the securing member 102 is introduced to the other side of the object 400A, 400B than the second end 102B of the securing member 102 is extended.

According to an embodiment the securing member 102 is arranged into the sheath 101 of the medical securing device 100 so that the first end 102A of it can be extended by the second securing member introduction device 113 to the first side of an object 400A, 400B and the second end of it 102B can be extended by the first securing member introduction device 103 to the second side of an object 400A, 400B. Thus the securing member 102 may be arranged to the sheath so that it forms a loop between the first and second ends 102A, 102B of it. The loop is advantageously arranged inside the sheath. Thus, according to an embodiment the medical securing device 100 comprises advantageously also a suitable opening 101D in the distal end 101B of the sheath 101 in order to allow also the loop to be extended from the sheath 101. The opening 101D is advantageously arranged to the distal end 101B of the sheath 101 so that when the first and second ends 102A, 102B of the securing member are extended by the securing member introduction devices the loop is then introduced around the proximal (upper) portion 400A of the object.

Advantageously both ends 102A, 102B or portions of the securing member 102 comprise shape memory material, whereupon they turn and/or twist due to shape memory material against and/or around each other when released by the securing member introduction devices 103, 113 and/or after penetration through the tissue 20. By this the securing member is coupled and secured to the object 400A, 400B and/or to the tissue 20.

FIGS. 5A-5D illustrate an example about the securing of an object 400 according to advantageous embodiment of the invention, where the object 400 may comprise a sleeve 401 at the rim portion 402 of the object 400 and advantageously at the outer (posterior) side of the loop shaped object. Thus, according to an embodiment the securing member 102 can be introduced through the sleeve 401 of the object and so that the object is secured by the securing member via said sleeve. Thus, when the end of the securing member or the securing member introduction device makes a hole to the tissue, the sleeve of the object will additionally seal the hole and thereby prevents possible leakages via the hole. Depending on the memory properties of the securing member and/or the directional movement of the securing member introduction device and securing member may be introduced so that the both ends 102A, 102B of the securing member are introduced to the same side of the object and so, that the ends are turned and/or twisted either against and around each other (see FIG. 5B) or towards and around the object (see FIG. 5D).

Figure 6A:
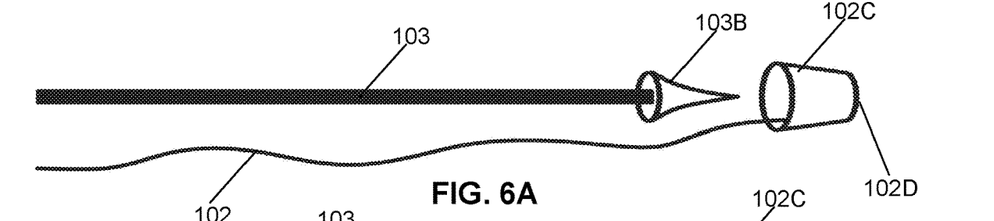
FIGS. 6A-6B illustrate examples of the end portions of the securing member and the securing member introduction device according to advantageous embodiment of the invention.
Figure 6B:
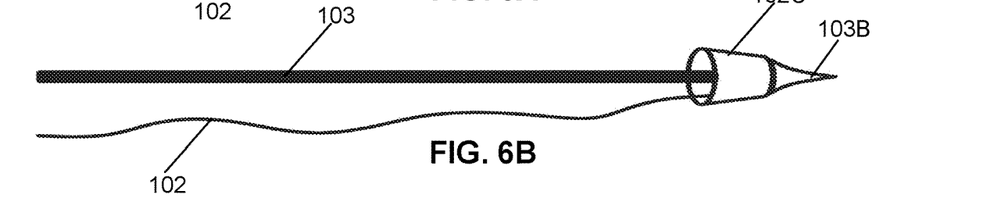

FIGS. 6A-6B illustrate examples of the end portions of the securing member and the securing member introduction device according to advantageous embodiment of the invention, where wherein the second 102B end of the securing member 102 comprises a cap like end 102C with opening 102D in it, The distal end 103B of the securing member introduction device 103 is configured to elongate through said opening, whereupon said distal end 103B of the securing member introduction device 103 is configured to function as a needle and according to an example comprises a needle head. The wire used for securing is advantageously attached to the cap end portion of the securing member.

FIGS. 7A-8E illustrate examples of the medical securing device with retrieval devices according to advantageous embodiment of the invention, wherein the retrieval device 104 comprises a proximal 104A and distal 104B ends. The distal end 104B, 114B is configured to extend from the sheath 101 and through the tissue, and configured to capture a portion of the second end 102B of the securing member 102 introduced through the tissue 20 and to secure the portion of the securing member 102 to the object 400A, 400B and/or to the tissue 20, as can be seen in FIGS. 7A-8E.

Figures 7A, 7B:
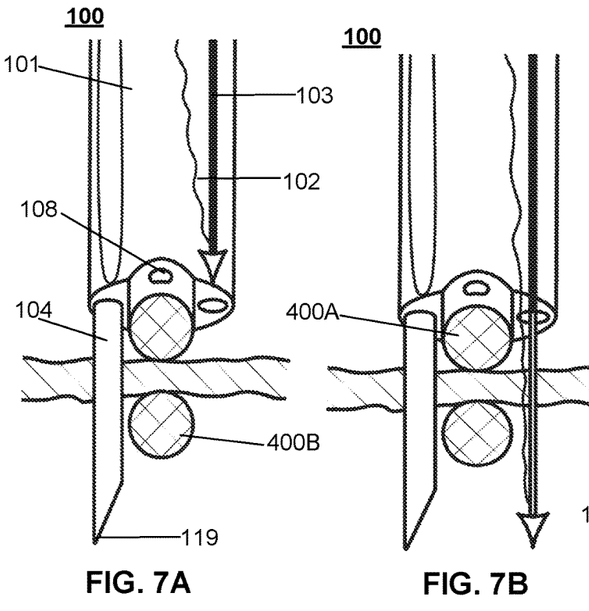
Figure 7C:
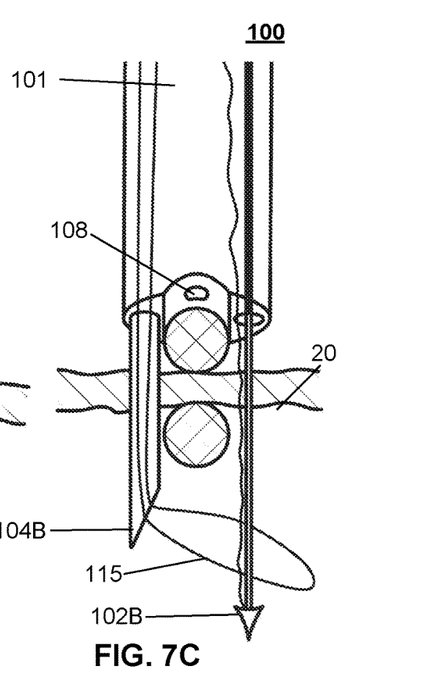
Figure 7D:
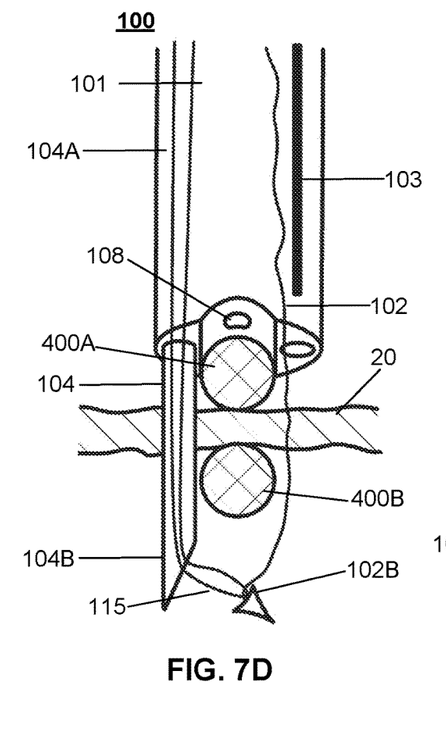
Figure 7E:
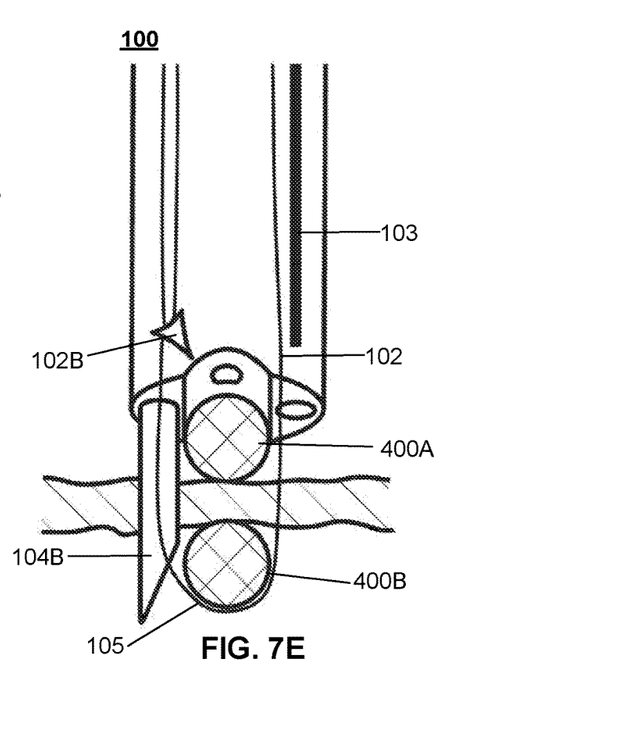
Figures 8A, 8B, 8C:
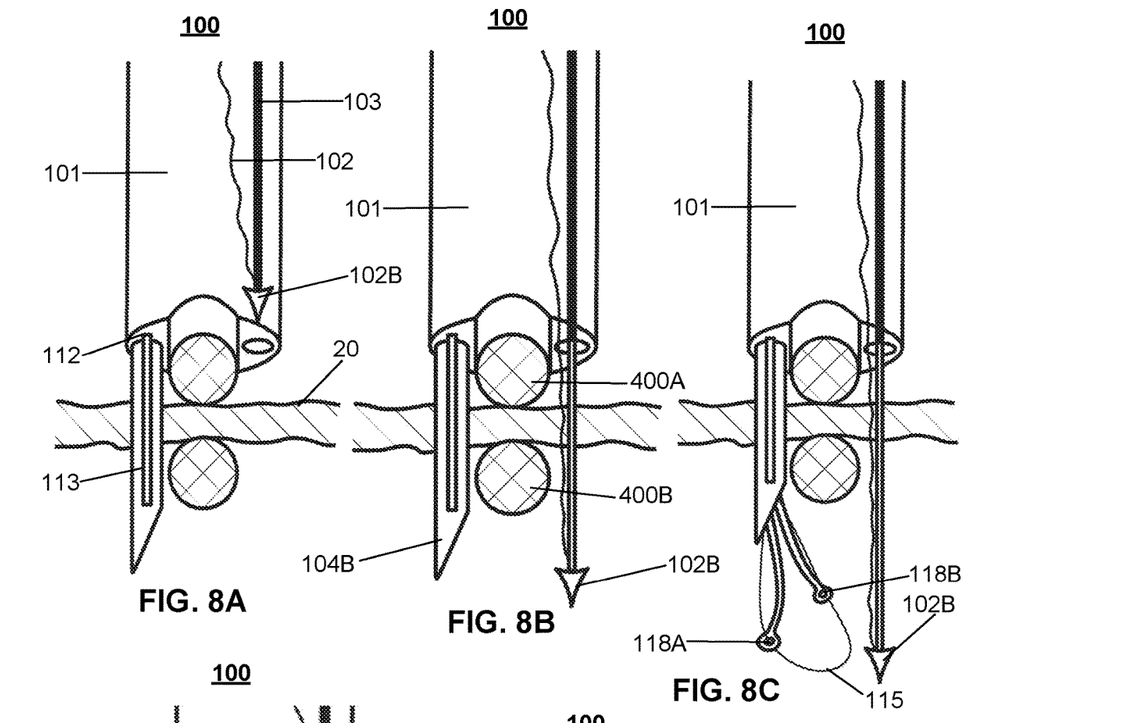
Figures 8D, 8E:
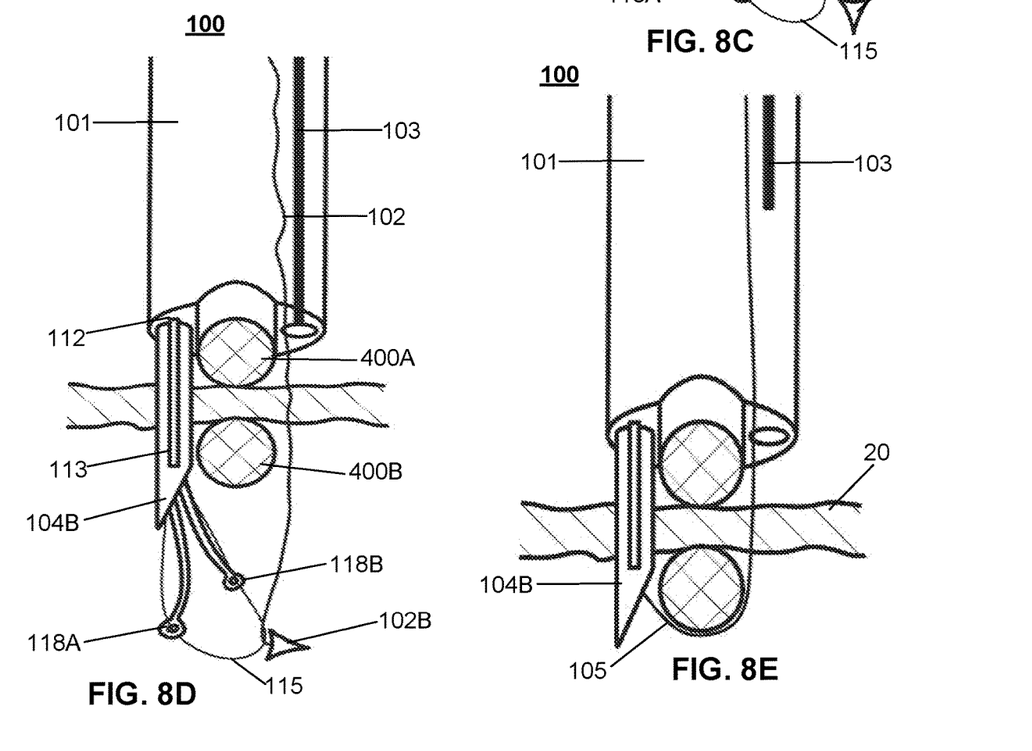

The retrieval device 104 and the second end 102B of the securing member 102 is advantageously extended beyond a distal part 400B of the object 400A, 400B in the longitudinal direction, whereupon the retrieval device 104 is configured to capture the portion of the securing member 102, after which the portion of the securing member can be pulled towards the retrieval device 104 to form a protrusion portion 105 or bridge 105 with said portion of the securing member 102 at least partially towards, over or across said distal part 400B of said object 400A, 400B between said securing member introduction device 103 and said retrieval device 104.

The retrieval device 104 may comprise a tip portion 119 configured for penetrating into or through the tissue 20, as is already discussed elsewhere in this document. In addition according to an embodiment the distal end 101B of the elongated sheath 101 comprises a guiding trail 112 and the distal portion of the securing member introduction device 103 and/or retrieval device 104 comprises a projection 113 as a counterpart for said guiding trail as can be seen in FIGS. 8A-8E, where the guiding trail and projection are thereby configured to guide the distal portion of the securing member introduction device 103 and/or retrieval device 104 to pierce the tissue 20 without substantive twisting around the longitudinal axis of the distal portion of the securing member introduction device 103 and/or retrieval device 104.

The retrieval device 104 may have different forms, as can also be seen e.g. in FIGS. 7A-8E, where in FIGS. 7A-7E the retrieval device 104 may comprise a loop 115, which can be positioned beneath the securing member introduction device 103 or the second portion of the securing member 102B and operated so that the second portion of the securing member 102B may then be introduced to the or through the loop. The second portion of the securing member 102B may comprise a proximal increased diameter portion 117B in order to ensure better catching of the securing member by the retrieval device.

In addition, according to an embodiment the retrieval device 104 according to an embodiment comprises radially displaceable arms 118A, 118B holding a loop 115. The radially displaceable arms 118A, 118B can be pushed out from the securing member introduction device 103 (catheter), whereupon the arms may be resiliently biased to diverge and thereby form an extended shape when displaced outside the sheath 101, as can be seen e.g. in FIGS. 8B-8D.

FIGS. 9-12 illustrate example additional features of the medical securing device according to advantageous embodiments of the invention.

Figure 9:
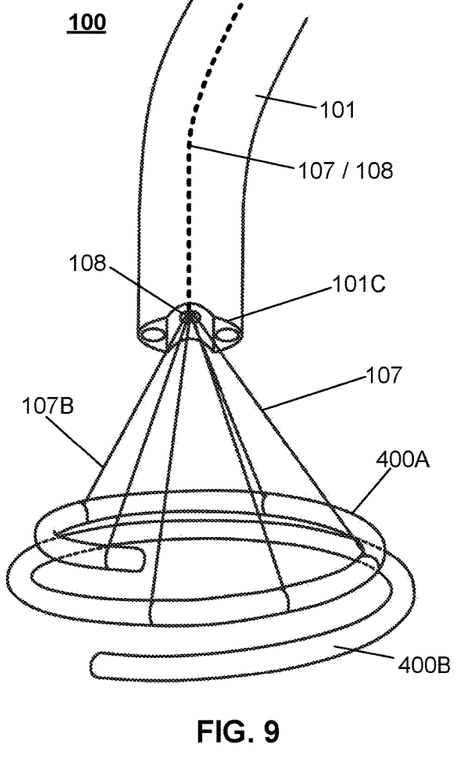

According to an embodiment the medical securing device 100, in particularly the sheath 101 may also comprise a conduit 108 between the proximal and distal ends 100A, 100B, 101A, 101B for receiving at least one guiding wire 107 coupled with the object to be secured (optional feature), as is described in FIG. 9, for example. If the object to be secured is provided with the guiding wire 107, the distal end 107B of is advantageously fixed to the object 400A, 400B so to guide the device along said guiding wire and to support a support portion 101C or a special recess 121 of the distal end 101B of the elongated sheath 101 to the object 400A, 400B to be secured.

In addition the medical securing device 100 may also comprise a cutting member for cutting the guiding wire 107 in the vicinity of the object 400A, 400B or the tissue 20. The device 100 may also comprise a cutting member for cutting the suture (as the securing member) by which the object is secured (not shown).

Figure 10:
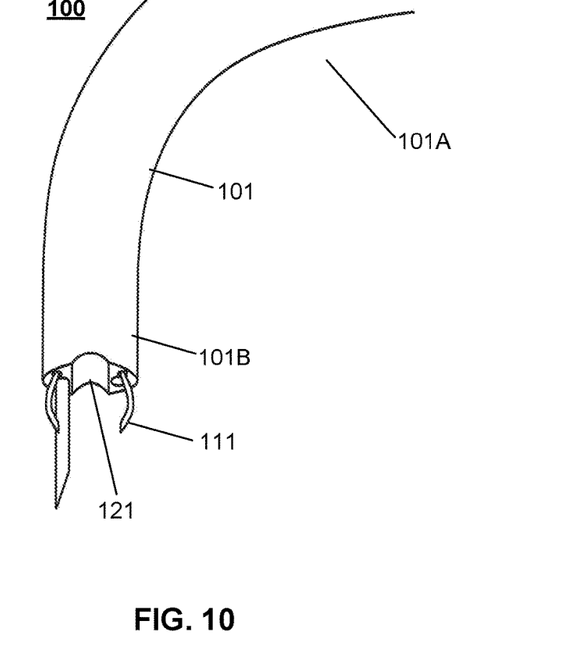

The medical securing device 100 or more precisely the distal end 101B of the elongated sheath 101 may also comprise a locking member 111, which is advantageously configured to lock the distal end 101B of the elongated sheath 101 to the object 400A, 400B or to the tissue 20, as can be seen in FIG. 10. The locking member 111 can be implemented e.g. by a finger or spring, and it might be made of or comprise shape memory material. It may be operable also from the proximal end of the elongated sheath so via operation arm 120, for example. In addition, as can be seen in FIGS. 10 and 11, the elongated sheath can be bendable (like a bendable and controllable catheter), whereupon it can be more easily directed into a right position, as well as that the securing member introduction device 103, 113 and retrieval device 104 can be retracted into the sheath 101 so that no tip portion is located outside the sheath 101, thereby avoiding or at least minimizing any damage to the artery or other anatomical structures of the patient in question during inserting the distal end of the medical securing device 100.

Figure 11:
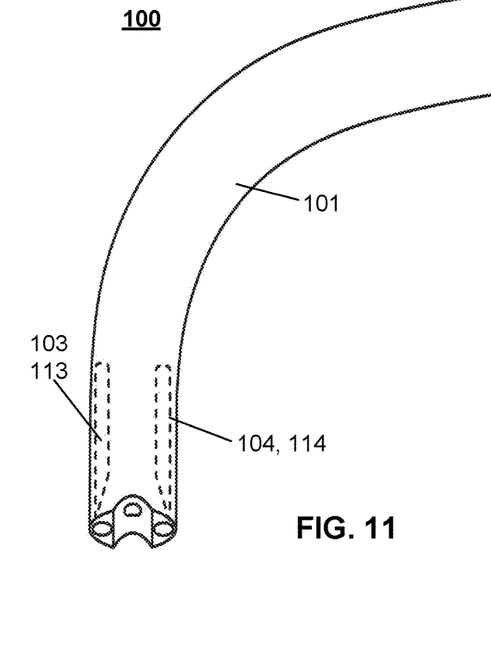

Moreover medical securing device 100, in particularly the sheath 101 may also comprise a conduit 108 between the proximal and distal ends thereof for introducing under pressure into the distal end 101B or to a support portion 101C, 121 of the elongated sheath 101 as is described in FIG. 11, but also 7A-7E. The under pressure is provided in order to suck and thereby to support the elongated sheath 101 or the support portion 101C or the recess 121 to the object 400A, 400B or to the tissue 20 via the force induced by the under pressure and/or for applying counterforce for the introduction movement 110 of the securing member 102.

According to an embodiment the medical securing device may comprise an actuating member 116 which comprises or at least is coupled with a spring and/or pre-stringed spring 128, pressure accumulator 129 or hydraulic or pneumatic arrangement 130 for facilitating or providing at least one direction of the movement of the back-and-forth movement of the securing member introduction device 103, 113 and/or retrieval device 104 (if used). For example, a first pre-stringed spring 128 or pressure accumulator 129 may trigger the out-movement of the securing member introduction device and/or retrieval device, whereupon the back-movement is triggered by the spring or pre-stringed spring 128. Naturally, also other combination can be applied and the force transmission to the actuating member 116 or the securing member introduction and/or retrieval devices can be applied via hydraulic arrangement 130 including also hydraulic hose 131.

The invention has been explained above with reference to the aforementioned embodiments, and several advantages of the invention have been demonstrated. It is clear that the invention is not only restricted to these embodiments, but comprises all possible embodiments within the spirit and scope of the inventive thought and the following patent claims. For example the object to be secured may be e.g. the cardiac implant (for example annuloplasty ring) device, but also other type of object can be secured, as is demonstrated and described in the description, In addition different kinds of securing members can be used, even if the suture is mentioned in the connection with most applications. In particularly it is to be understood that the invention can be applied as a catheter-operated or cannula-operated medical securing device and for securing the cardiac implant device into an annulus of a heart valve, such as a mitral valve or tricuspid valve, comprised of valve tissue and including the annulus and a plurality of leaflets. However, the principle of the invention can also be applied for an open-heart operated medical securing device, as well as securing also other object as only the cardiac implant devices, such as tissue or skin transplant beneath the skin or the like. In addition the invention can also be used for securing an artificial heart valve, for example.

The features recited in dependent claims are mutually freely combinable unless otherwise explicitly stated.

The invention claimed is:

1. A medical securing device for securing an object with a securing member into a tissue, the medical securing device comprising:
the securing member comprising first and second ends;
an elongated sheath comprising proximal and distal ends;
a securing member introduction device comprising proximal and distal ends; and
a retrieval device having proximal and distal ends,
wherein said distal end of the securing member introduction device is configured to extend a second end of the securing member from the sheath and introduce with the tissue via an introduction movement and said distal end of the retrieval device is configured to extend from the sheath and through a first side of tissue to a second side of tissue so that the distal end of the retrieval device reaches a tissue-free area,
further wherein the distal end of the retrieval device is configured to capture a portion of the second end of the securing member introduced through the tissue to the tissue-tree area and to secure the portion of the securing member to the object or to the tissue, wherein the elongated sheath comprises a conduit between the proximal and distal ends thereof for introducing under pressure into the distal end of the elongated sheath in order to suck and thereby to support and secure the conduit and thereby also the elongated sheath directly to the object to minimize the movement between the elongated sheath and the object.

2. The medical securing device of claim 1,
wherein the second end of the securing member is configured to function as a needle and thereby to penetrate the tissue when extended from the sheath by said distal end of the securing member introduction device or
wherein the second end of the securing member comprises a cap-like end with an opening and the distal end of the securing member introduction device is configured to elongate through said opening, whereupon said distal end of the securing member introduction device is configured to function as a needle.

3. The medical securing device of claim 1, wherein at least the second end or a second portion of the securing member comprises shape memory material, whereupon the at least the second end or the second portion of the securing member is configured to be twisted due to shape memory material when released by the securing member introduction device and thereby coupled with said object and securing a portion of the securing member to the object or to the tissue.

4. The medical securing device of claim 1, wherein the distal end of the securing member introduction device is mechanically coupled with the securing member and arranged to be released from the securing member by directional guiding or guidance or by turning said securing member introduction device around the longitudinal axis or the securing member introduction device a certain amount.

5. The medical securing device of claim 1, wherein at least the first end or a first portion of the securing member comprises shape memory material, whereupon the at least the first end or the first portion of the securing member is configured to be twisted due to shape memory material when released by tile securing member introduction device and thereby coupled with said object and securing the portion of the securing member to the object or to the tissue.

6. The medical securing device of claim 1, wherein the second end or the first end of the securing member comprises an increased diameter portion.

7. The medical securing device of claim 6, wherein tile second end or the first end of the securing member is configured to be compressible when introduced through the tissue or elongating to a certain predetermined direction after penetration the tissue.

8. The medical securing device of claim 1, wherein the second end or the first end or the securing member comprises a needle portion in order to allowing penetration of said end of the securing member to the or through the tissue.

9. The medical securing device of claim 1, wherein the medical securing device comprises a second securing member introduction device comprising proximal and distal ends, wherein said distal end of the second securing member introduction device is configured to extend the first end of the securing member from the sheath and to the or through the tissue so to secure the portion of the securing member to the object or to the tissue.

10. The medical securing device of claim 9, wherein at least tile second end or a second portion or the first end or a first portion of the securing member comprises shape memory material, whereupon the at least the second end or the second portion or the first end or the first portion of the securing member is configured to be twisted due to shape memory material against each other or around the object when released by the securing member introduction device and after penetration through the tissue and thereby coupled with said object and securing the portion of the securing member to the object or to the tissue.

11. The medical securing device of claim 1, wherein the medical securing device is configured to extend the retrieval device and the second end of the securing member beyond a distal part of the object in said longitudinal direction, and the retrieval device is configured to capture the portion of the securing member, whereby the portion of the securing member can be pulled towards the retrieval device to form a protrusion portion or bridge with said portion of the securing member at least partially towards, over or across said distal part of said object between said securing member introduction device and said retrieval device.

12. The medical securing device of claim 1, wherein said retrieval device comprises a tip portion configured for penetrating into or through the tissue.

13. The medical securing device of claim 1, wherein the elongated sheath comprises a conduit between the proximal and distal ends thereof for receiving at least one guiding wire, a distal end of the guiding wire being fixed to the object and thereby for guiding a support portion of the distal end of the elongated sheath along said guiding wire and to support a support portion to the object.

14. The medical securing device of claim 13, wherein the elongated sheath together with the guiding wire of the object provides a system for applying counterforce for the introduction movement of the securing member to the object and thereby for securing or supporting or stabilizing the support portion of the distal end of the elongated sheath to the object.

15. The medical securing device of claim 1, wherein the distal end of the elongated sheath comprises a locking member configured to lock the distal end of the elongated sheath to the object or to the tissue or for allowing the capturing and positioning the object.

16. The medical securing device of claim 1, wherein the distal end of the elongated sheath comprises a guiding trail and a distal portion of the securing member introduction device comprises a projection as a counterpart for said guiding trail, where said guiding trail and projection are thereby configured to guide said distal portion of the securing member introduction device to pierce the tissue without substantive twisting around the longitudinal axis of the distal portion of the securing member introduction device.

17. The medical securing device of claim 1, wherein the distal end of the elongated sheath comprises a guiding trail and a distal portion of the retrieval device comprises a projection as a counterpart for said guiding trail, where said guiding trail and projection are thereby configured to guide said distal portion of the retrieval device to pierce the tissue without substantive twisting around the longitudinal axis of the distal portion of the retrieval device.

18. The medical securing device of claim 1, wherein the proximal end of the elongated sheath comprises an operation arm for moving the distal end of the securing member introduction device thereby introducing the securing member to the object or to the tissue thereby introducing the securing member and thereby capturing a portion of the securing member and securing the portion of the securing member to the object or to the tissue.

19. The medical securing device of claim 1, wherein the proximal end of the elongated sheath comprises an operation arm for moving the distal end of the retrieval device and thereby capturing a portion of the securing member and securing the portion of the securing member to the object or to the tissue.

20. The medical securing device or claim 1, wherein the distal end of the securing member introduction device Is configured to introduce at least portion of the securing member to an upper portion or lower portion of the object and/or into the tissue.

* * * * *